United States Patent [19]  [11]  4,251,456
Brooks  [45]  Feb. 17, 1981

[54] METHOD FOR TREATING EFFLUENT GAS FROM SULFONATION PROCESS

[75] Inventor: Burton Brooks, Bellevue, Wash.

[73] Assignee: The Chemithon Corporation, Seattle, Wash.

[21] Appl. No.: 24,895

[22] Filed: Mar. 29, 1979

[51] Int. Cl.³ .................. C07C 143/24; C07C 143/02
[52] U.S. Cl. ............................ 260/505 R; 260/513 T; 260/504 R
[58] Field of Search ............ 260/513 T, 505 R, 504 R

[56] References Cited
U.S. PATENT DOCUMENTS 4,036,875  7/1977  Bröstrom ........................ 260/513 T

OTHER PUBLICATIONS

Kirk–Othmer "Encyclopedia of Chem. Tech." (1969) pp. 465–473.

Primary Examiner—Alan Siegel

Attorney, Agent, or Firm—Merriam, Marshall & Bicknell

[57] ABSTRACT

A relatively large amount of $SO_2$ effluent gas from a sulfonation process is converted to $SO_3$ and recycled back to the sulfonation process as part of the $SO_3$ sulfonating agent. The rest of the $SO_3$ used as the sulfonating agent is derived from a sulfur burner located downstream of the sulfonation operation and in the recycle path of the $SO_2$ in the effluent gas. Hydrocarbons in the effluent gas are converted to $CO_2$ and $H_2O$ in the sulfur burner. The $H_2O$ and $SO_3$ are removed from the gas stream at an $SO_3$ absorber which forms rich oleum from which the $SO_3$ is subsequently removed for use in the sulfonation operation, leaving lean oleum which is used at the $SO_3$ absorber to remove $H_2O$ and $SO_3$ from the gas stream. Gases leaving the $SO_3$ absorber include some $SO_3$ and are passed through an $H_2SO_4$ absorber along with water and lean oleum to produce concentrated $H_2SO_4$.

15 Claims, 2 Drawing Figures

METHOD FOR TREATING EFFLUENT GAS FROM SULFONATION PROCESS

BACKGROUND OF THE INVENTION

This invention relates to a process for sulfonating liquid organic feed stocks and more particularly it relates to a sulfonation process, using sulfur trioxide ($SO_3$) as the sulfonating agent, in which provision is made for treating the effluent gases from the sulfonation process to recover for reuse any $SO_3$ or $SO_2$ therein and to eliminate therefrom noxious fumes before discharging the gases to the atmosphere.

Sulfonation of a wide variety of organic liquid feedstocks, and particularly relatively highly refined hydrocarbons, such as "detergent alkylate", benzene, toluene and the like, has been practiced conventionally for many years. Although several different sulfonating agents, such as concentrated sulfuric acid, oleums of various strengths, and $SO_3$ have been used, treatment with $SO_3$ is usually the process of choice, since the reaction is essentially instantaneous and proceeds to completion, thus minimizing equipment requirements for a given rate of production.

In a common process for sulfonation with $SO_3$, the $SO_3$ in vapor form is mixed with dry air and brought into contact with the liquid feed stock to produce a sulfonic acid which is then neutralized to form sulfonate. Although the desired sulfonated product is quickly and simply obtained, the effluent gases from the sulfonation step present a disposal problem, since they contain, in addition to excess $SO_3$ not consumed in the sulfonation step, vapors of the liquid feed stock, as well as $SO_2$ formed during the sulfonation step and perhaps some residual $SO_2$ introduced into the sulfonation process with the $SO_3$. Generally, the amount of $SO_2$ in the effluent gases is sufficiently small that it can be removed from the effluent gases by scrubbing, without economic disadvantage. For example, with some relatively highly refined hydrocarbons, the $SO_2$ content of the effluent gas is only 2-3 wt. % of the $SO_3$ introduced at the sulfonation step.

In the case of sulfonating crude oil or gas oil, however, the $SO_2$ content of the effluent gas can be in the range 5-15 wt. % of the $SO_3$ introduced at the sulfonation step. "Gas oil" is a term conventionally used in the petroleum industry to describe a hydrocarbon friction near the bottom "cut" in the atmospheric distillation of petroleum, or its equivalent.

Therefore, in the sulfonation of crude oil or gas oil, or in the sulfonation of relatively highly refined hydrocarbon at very large rates of sulfonation (e.g., 50 to 100 million pounds of sulfonate per year), the amount of $SO_2$ (and $SO_3$) in the effluent gases from the sulfonation step can be quite large, and this amount represents an excessive economic loss unless the $SO_2$ (and $SO_3$) in the effluent gases is recovered for re-use in the sulfonation step.

Recent proposals for tertiary recovery of petroleum involve the use of sulfonated petroleum fractions which are injected into wells to increase the recovery of petroleum trapped within the rock or sand formation. For such use, large quantities of sulfonated petroleum fractions, typically having a molecular weight of 300-1000, are necessary. These large quantities are produced by $SO_3$ sulfonation at very large rates, and, in doing so, substantial quantities of $SO_2$ are formed.

Moreover, in view of the increasingly rigorous standards relating to atmospheric pollution, a sulfonation effluent gas stream containing substantial concentrations of $SO_2$ and $SO_3$ cannot be discharged directly to the atmosphere, and, particularly in the case of a plant treating large volumes of feed stocks, disposal of the effluent gases from the sulfonation step presents a serious problem.

SUMMARY OF THE INVENYION

The effluent gas from the sulfonation step contains $SO_2$, $SO_3$, residual air and hydrocarbon mist and vapor. In accordance with the present invention, the $SO_2$ and $SO_3$ is recovered for further use by feeding the effluent gas to a sulfur burner along with make-up sulfur. The sulfur burns to $SO_2$ and is catalytically oxidized to $SO_3$, along with the residual $SO_2$. The hydrocarbon materials burn to carbon dioxide and water.

The resulting $SO_3$ can be recycled back to the sulfonation step, but the water should not be recycled as it would react with the $SO_3$ to form $H_2SO_4$, and the $SO_3$ would not be available to enter into the sulfonation step, which is undesirable. The water is removed before the sulfonation step with an $SO_3$ absorption step performed on the gases downstream of the sulfur burner (said gases comprising $SO_3$ and $H_2O$ plus $CO_2$ and residual $O_2$ and $N_2$).

In the $SO_3$ absorption step, the catalytically oxidized gases from the sulfur burner are contacted with lean oleum. Some of the $SO_3$ is absorbed by the lean oleum to form rich oleum. The water reacts with some of the $SO_3$ to form sulfuric acid which in turn reacts with additional $SO_3$ to form oleum. The carbon dioxide, along with oxygen and nitrogen from the residual air, are unaffected by the oleum absorption step and can be discharged to the atmosphere without creating pollution problems.

The rich oleum is then desorbed to produce $SO_3$ for the sulfonation process and lean oleum, and the lean oleum from the desorption process is recycled to the $SO_3$ absorption step. Some sulfuric acid is formed as a byproduct and is removed from the system, and some of the water formed by burning the hydrocarbon mist may enter into this sulfuric acid. Because the sulfur dioxide is reoxidized and recycled, the use of expensive alkaline agents to remove substantial amounts of $SO_2$ by scrubbing is avoided.

The catalytic oxidizing step used to oxidize the $SO_2$ to $SO_3$, and the immediately preceding sulfur burning step are both performed downstream of the sulfonating step and constitute the steps from which is derived all the $SO_3$ with which the liquid organic feed stock is sulfonated.

Other features and advantages are inherent in the method claimed and disclosed or will become apparent to those skilled in the art from the following detailed description in conjunction with the accompanying diagramatic drawings.

DETAILED DESCRIPTION

Figure 1:
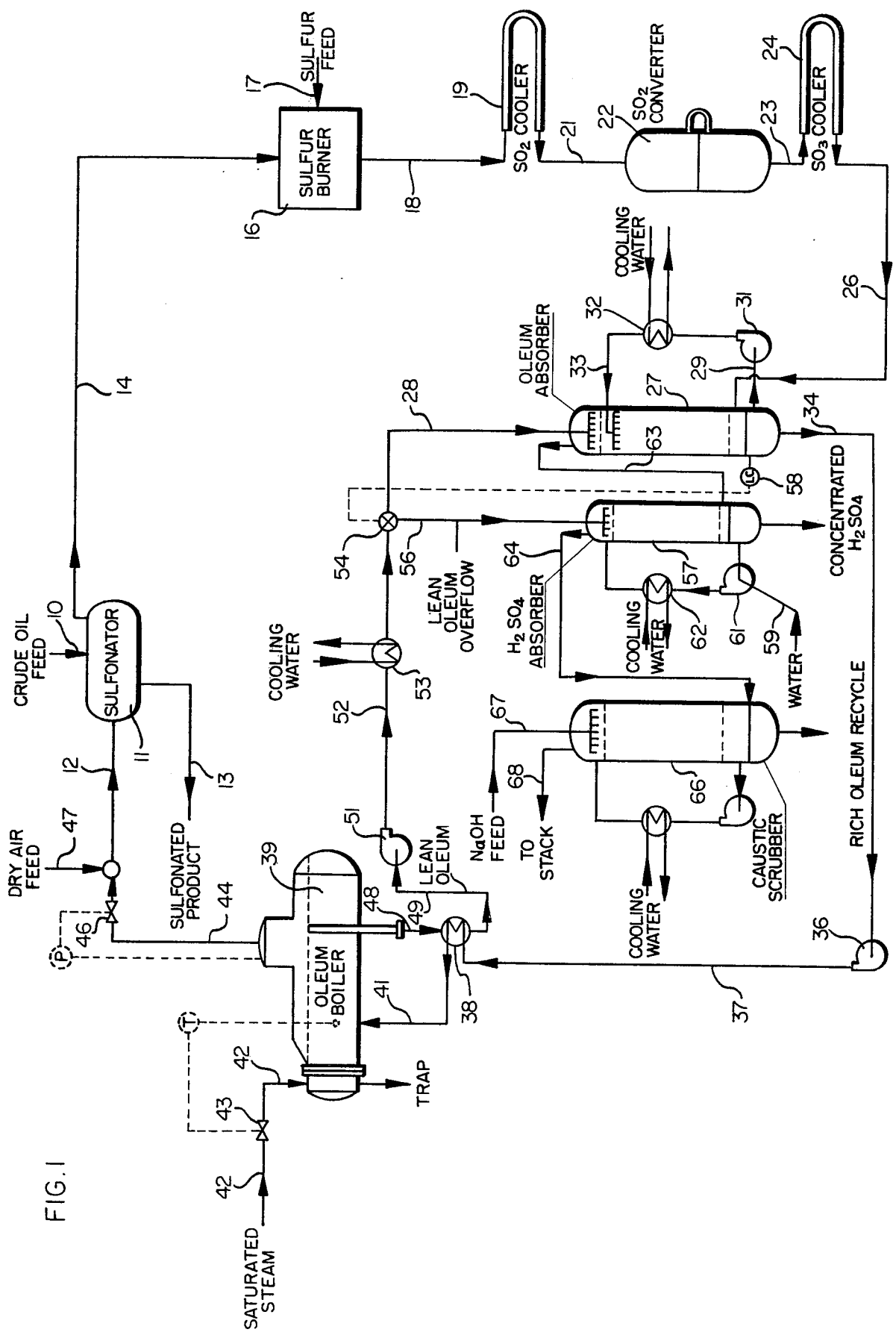
FIG. 1 is a flow sheet of a continuous process embodying the method of the invention.

As shown in FIG. 1, a stream of crude oil or other feed is introduced through line 10 to sulfonator 11, to which is introduced through line 12 a mixture of $SO_3$ and dry air, typically containing about 3–15% by volume of $SO_3$, e.g., 8–10%. In sulfonator 11, sulfonation proceeds in conventional fashion, yielding a desired liquid sulfonation product (e.g., sulfonic acid) which is recovered through line 13 for eventual neutralization to produce a sulfonate, for example.

The effluent gases from sulfonator 11, optionally after passage through a liquid deentrainment device such as a cyclone separator (not shown), pass through line 14 to a conventional sulfur burner 16, to which makeup sulfur is supplied as necessary through line 17. The gas stream entering sulfur burner 16 contains essentially all of the oxygen and nitrogen present in the dry air fed to sulfonator 11 and, in addition, unreacted $SO_3$, typically up to about 1.5% by volume, $SO_2$ formed during the sulfonation step, typically in a concentration of about 0.5–2% by volume, and untreated vapors of the liquid feed stock introduced into sulfonator 11 through line 10. Some of these vapors may be removed by a mesh filter or electrostatic precipitator (not shown) located upstream of sulfur burner 16.

In sulfur burner 16, typically operated at a temperature of about 1,100°–1,500° F. (593°–815° C.) in conventional fashion, the sulfur feed 17 burns to form $SO_2$, and the entrained hydrocarbon liquid entering through gas line 14 burns to form $CO_2$ and water vapor, while the $SO_2$ and $SO_3$ entering through gas line 14 remain essentially unchanged.

The gases produced in sulfur burner 16, leaving through line 18, pass through $SO_2$ cooler 19, wherein the temperature of the gas stream is lowered to about 850°–1,100° F. (454°–593° C.) in conventional fashion, and enter $SO_2$ converter 22 via line 21. In $SO_2$ converter 22, $SO_2$ in the gas stream reacts with oxygen (from the air originally supplied upstream at sulfonator 11) in the presence of a suitable catalyst such as vanadium oxide, to form $SO_3$, in conventional fashion. The efficiency of conversion is conventionally such that about 98% of the $SO_2$ entering is converted to $SO_3$.

The gases leaving $SO_2$ converter 22 comprise $SO_3$, some residual $SO_2$, $CO_2$, $H_2O$ and residual $O_2$ and $N_2$. These gases pass, via line 23, to $SO_3$ cooler 24, in which the temperature of the stream is reduced to a temperature above the dew point of $H_2SO_4$ (e.g., 550° F. (288° C.)) to prevent condensation of sulfuric acid in the stream. Leaving $SO_3$ cooler 24, the cooled gases pass through line 26 to the base of $SO_3$ absorber tower 27, through which the gases pass upwardly against a downwardly-flowing stream of lean oleum entering the top of the tower through line 28. A recycle sidestream is drawn from the base of tower 27 through line 29, pump 31 and heat exchanger 32 wherein it is cooled, and delivered to the top of tower 27 through line 33. The rate of recycle and the temperature of the cooling water used in heat exchanger 32 are coordinated to maintain a temperature at the base of tower 27 within the range of about 100°–150° F. (38°–66° C.) e.g., 140° F. (60° C.), to facilitate absorption of $SO_3$ into the stream of lean oleum 28 entering the top of $SO_3$ absorber tower 27.

The process conditions in $SO_3$ absorber 27 are adjusted such that lean oleum 28, which has typically an $SO_3$ content of about 18–25% by weight when it enters the top of tower 27, absorbs sufficient $SO_3$ to reach about 20–30% $SO_3$ by weight as it leaves the bottom of $SO_3$ absorber tower 27 via line 34. The $SO_3$-rich oleum is conveyed via pump 36 and line 37 through heat exchanger 38, wherein it is heated, and enters oleum boiler 39 through line 41. The oleum in boiler 39 is heated by appropriate means such as saturated steam entering through line 42, the quantity of steam being regulated by temperature-controlled valve 43 to maintain an appropriate temperature within the boiler. The heated oleum within boiler 39 evolves $SO_3$ vapors which leave the boiler through line 44, the rate being regulated by pressure-controlled valve 46. After addition of an appropriate amount of dry air through line 47, the mixture of air and $SO_3$ is passed to sulfonator 11 through line 12, as previously described.

The liquid phase within oleum boiler 39, which has been depleted of some of its $SO_3$ to a level below that in the rich oleum stream (e.g., to 18–25% $SO_3$ by weight in the depleted oleum), leaves via line 48, and, after heat exchange with entering $SO_3$-rich oleum in exchanger 38, passes through line 49, pump 51, line 52 and heat exchanger 53 (wherein it is cooled) to proportioning valve 54, wherein a split in the stream is made. A first portion of the depleted or lean oleum passes through line 28 to the top of $SO_3$ absorber 27. A second portion or sidestream of lean oleum (lean oleum overflow) flows via line 56 to the top of $H_2SO_4$ absorber tower 57. The relative proportions of the two oleum streams (i.e., line 28 to $SO_3$ absorber 27 and line 56 to $H_2SO_4$ absorber 57) are controlled by level control 58 to maintain a desired level at the base of tower 27.

In $H_2SO_4$ absorber 57, the lean oleum entering through line 56 is diluted by the addition of water through line 59 to form concentrated sulfuric acid into which is absorbed $SO_3$ from the upwardly flowing stream of gases entering the bottom of $H_2SO_4$ absorber 57 through line 63. A portion of this concentrated $H_2SO_4$ is recycled by pump 61 through heat exchanger 62, wherein it is cooled, to the top of $H_2SO_4$ absorber 57 wherein it descends against the upwardly-flowing stream of gases from $SO_3$ absorber 27. The strength of the concentrated $H_2SO_4$ at the bottom of $H_2SO_4$ absorber 57 is approximately 96–98%. Treatment of the gases from $SO_3$ absorber 27 in this manner at absorber 57 is effective in removing substantially all of the residual $SO_3$ content from gas stream 63.

In some circumstances, it may be acceptable to discharge the gas stream leaving $H_2SO_4$ absorber 57 via line 64 directly to the atmosphere. Gas stream 64 does, however, contain a small concentration of $SO_2$ which can, if necessary or desirable, be scrubbed in caustic scrubber 66 with an aqueous solution of NaOH, entering through line 67, in conventional fashion. The off-gases leaving caustic scrubber 66 via line 68, now containing essentially no noxious components, can be discharged to the atmosphere without creating any pollution problems.

An alternative method of removing the last traces of $SO_2$ is to reheat gas stream 63 to 850° F. (454° C.) and pass it through an additional catalytic converter stage, much like converter 22, where 98% of the residual $SO_2$ is converted to $SO_3$. The gases leaving the converter are then cooled and fed to $H_2SO_4$ absorber 57, forming $H_2SO_4$. The gas leaving absorber 57 through line 64 has such a low $SO_2$ content that it can be discharged directly to the atmosphere.

As previously noted, during the operation of $SO_3$ absorber 27, the $SO_3$ content of rich oleum stream 34 leaving the absorber is generally within the range 20-30% by weight. 30% is a practical maximum for the SO$_3$ content in oleum. In general, it will usually be found desirable, in the interests of economy, to maintain the concentration of SO$_3$ in rich oleum stream 34 at as low a level as feasible within that range, since a relatively high SO$_3$ concentration in rich oleum stream 34 will be accompanied by the production of a relatively large amount of concentrated H$_2$SO$_4$ at absorber 57.

More specifically, assume a given amount of SO$_3$ introduced into absorber 27 through line 26. In order to produce a relatively high SO$_3$ concentration in the oleum in line 34 there must be a relatively smaller proportion of lean oleum introduced into absorber 27 through line 28 than would be introduced to make a relatively low SO$_3$ concentration in the oleum in line 34. The lower the proportion of lean oleum directed into line 28 at valve 54, the higher the proportion of lean oleum directed into line 56 leading to H$_2$SO$_4$ absorber 57; and, the higher the proportion of lean oleum entering H$_2$SO$_4$ absorber 57, the larger the amount of concentrated byproduct H$_2$SO$_4$ formed at H$_2$SO$_4$ absorber 57.

Normally, H$_2$SO$_4$ is not as desirable a product, from a practical or economical standpoint as is oleum. Therefore, to minimize H$_2$SO$_4$ production and maximize oleum production, oleum would be produced at SO$_3$ absorber 27 at a concentration somewhat less than 30%, although still within the range 20-30%. However, if the by-product H$_2$SO$_4$ made at absorber 57 can be used in an economical manner there will be no penalty in maintaining a high concentration of SO$_3$ (e.g., 30%) in rich oleum stream 34, because the accompanying production of large amounts of concentrated H$_2$SO$_4$ can be accommodated.

In the operation of oleum boiler 39 it will usually be desirable to avoid excessively depleting the SO$_3$ content of lean oleum stream 48, since the boiling point of the oleum in boiler 39 increases as the SO$_3$ content is reduced, thereby requiring the use of greater amounts of stream or other heat supply to the boiler. In addition, the corrosivity of the oleum increases as the SO$_3$ content drops, a factor which may cause excessive corrosion of equipment. In general, therefore, it will usually be found desirable to maintain the SO$_3$ content of the lean oleum in boiler 39 within the range of about 18-25% by weight.

In summary, the SO$_3$ content in rich oleum stream 34 is somewhere in the range 20-30%, while the SO$_3$ content in lean oleum stream 48 is less than that of the rich oleum stream but is at least about 18% by weight of dissolved SO$_3$. Thus, for example, if the SO$_3$ content of the rich oleum stream is 30%, the SO$_3$ content of the lean oleum stream typically would be 25%, but, conceivably, it could be as high as 29%.

Figure 2:
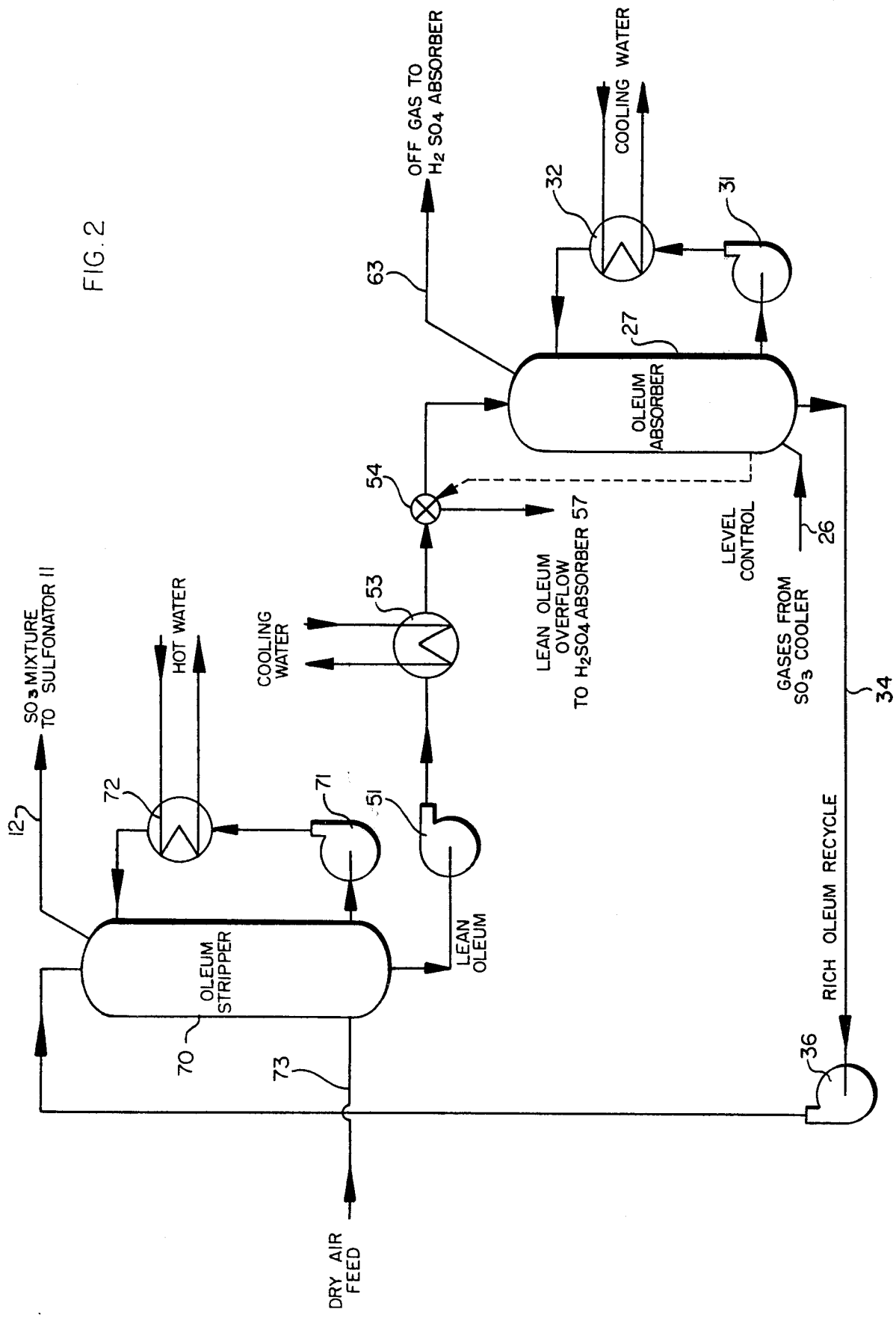
FIG. 2 is a flow sheet of an alternative step in the process of FIG. 1, demonstrating a different method of desorbing or stripping dissolved $SO_3$ from the $SO_3$-rich oleum employed therein.

In FIG. 2 there is depicted an alternative embodiment of the invention in which SO$_3$ is stripped from rich oleum by contact with dry air in oleum stripper 70, rather than by boiling the SO$_3$-rich oleum in a boiler as shown in FIG. 1. In FIG. 2, except for oleum stripper 70, and its associated equipment (recycle pump 71 and heat exchanger 22) all of the other equipment duplicates that in FIG. 1. Dry air fed by line 73 to the base of oleum stripper 70 strips SO$_3$ from the heated oleum to produce a mixture of SO$_3$ and air which is passed by line 74 to sulfonator 11 (FIG. 1), as previously described.

The foregoing detailed description has been given for clearness of understanding only, and no unnecessary limitations should be understood therefrom as modifications will be obvious to those skilled in the art.

What is claimed is:

1. In the method which comprises sulfonating a liquid organic feed stock by contacting said liquid feed stock with a gas mixture containing air and SO$_3$ derived from a sulfur burning step and separating the resulting liquid sulfonated product from a gas phase containing residual air, unreacted SO$_3$, vapors from said feed stock and SO$_2$, the steps of:
   (1) burning sulfur in the presence of said separated gas phase to produce additional SO$_2$;
   (2) catalytically treating the gas phase produced in step (1) to convert SO$_2$ contained therein to SO$_3$, said sulfur burning and catalytic treating steps being performed downstream of said sulfonating step and constituting said sulfur burning step from which is derived said SO$_3$ with which said liquid organic feed stock is sulfonated;
   (3) treating the gas from step (2) with lean oleum to absorb in said oleum a substantial proportion of the SO$_3$ contained therein, producing SO$_3$-rich oleum;
   (4) desorbing SO$_3$ from said SO$_3$-rich oleum to produce SO$_3$ vapor and lean oleum;
   (5) mixing the SO$_3$ vapor produced in step 4 with air;
   (6) contacting said liquid organic feed stock with the mixture of air and SO$_3$ produced in step (5);
   (7) using at least a portion of the lean oleum produced in step (4) for absorbing SO$_3$ in step (3);
   (8) removing SO$_3$ remaining in the gas after step (3) and then discharging said gas to the atmosphere.

2. In the method of claim 1 wherein:
   said vapors from said feed stock are converted to CO$_2$ and H$_2$O vapor at said sulfur burning step (1),
   and said method comprises removing said H$_2$O vapor from the process, before step (6), by reacting the H$_2$O with some of said SO$_3$ from step (2) to produce oleum, at step (3);
   said CO$_2$ being discharged to the atmosphere after step (3).

3. In the method of claim 1 wherein said SO$_3$ vapor is produced in said desorbing step (4) by heating said SO$_3$-rich oleum.

4. In the method of claim 1 wherein said steps of desorbing and mixing with air (4) and (5) are performed simultaneously by stripping SO$_3$ vapor from said SO$_3$-rich oleum with a stream of air.

5. In the method of claim 1 wherein said SO$_3$-rich oleum contains about 20-30% by weight of dissolved SO$_3$.

6. In the method of claim 1 wherein said lean oleum contains less dissolved SO$_3$ than said rich oleum and at least about 18% by weight of dissolved SO$_3$.

7. In the method of claim 1 wherein said feedstock is a petroleum fraction.

8. In the method of claim 1 wherein:
   the SO$_2$ content of said separated gas phase is greater than about 5% by weight of the SO$_3$ contacting said liquid feed stock.

9. In the method of claim 1 wherein:
   said liquid feed stock is selected from the group consisting of crude oils and gas oils.

10. A method as recited in claim 1 and comprising:
    dividing said lean oleum into first and second portions;
    using said first portion of the lean oleum for absorbing SO$_3$ in said gas-treating step (3);

adding water to said second portion of lean oleum to produce concentrated sulfuric acid and using said concentrated sulfuric acid at said $SO_3$-removing step (8) to absorb any $SO_3$ remaining in the gas treating step (3);

and discharging to the atmosphere the gas remaining after said water-adding step.

11. In the method of claim 10 where the gas remaining after said water-adding step is washed with caustic to remove acidic components prior to being discharged to the atmosphere.

12. In the method of claim 10 wherein a portion of the concentrated sulfuric acid produced in said water-adding step is recycled at that step to absorb said $SO_3$.

13. In the method of claim 1 wherein:

said vapors from said feed stock are converted to $CO_2$ and $H_2O$ vapor at said sulfur burning step (1), said $CO_2$ and said $H_2O$ vapor being part of the gas from step (2);

and said method comprises separating said $H_2O$ vapor and said $CO_2$ from said $SO_3$ in said gas from step (2), so that the $SO_3$ produced at step (4) is substantially free of $H_2O$ vapor and $CO_2$ at the time of said contacting step (6).

14. A method as recited in claim 1 and comprising:

removing residual $SO_2$ from said gas, after said $SO_2$ removing step (8) and before discharging said gas to the atmosphere.

15. A method as recited in claim 1 and comprising:

removing $H_2O$ vapor from the gas from step (2) at the same time as said $SO_3$ is absorbed from said gas.

* * * * *

UNITED STATES PATENT AND TRADEMARK OFFICE
CERTIFICATE OF CORRECTION

PATENT NO. : 4,251,456
DATED : February 17, 1981
INVENTOR(S) : Burton Brooks

It is certified that error appears in the above-identified patent and that said Letters Patent are hereby corrected as shown below:

Column 5, line 41, "stream" should be --stream--.

Column 6, line 35, "step (1)," should be --step (1);--.

Column 8, line 11, "after said $SO_2$" should be --after said $SO_3$--.

Signed and Sealed this

Twelfth Day of May 1981

[SEAL]

Attest:

RENE D. TEGTMEYER

Attesting Officer     Acting Commissioner of Patents and Trademarks